United States Patent
Brown et al.

(10) Patent No.: US 11,174,214 B2
(45) Date of Patent: Nov. 16, 2021

(54) DEOXYBENZOIN MONOMERS AND BRANCHED POLYMERS PREPARED THEREFROM

(71) Applicant: University of Massachusetts, Boston, MA (US)

(72) Inventors: Moira Caitlin Brown, Chicago, IL (US); Elizabeth Ganz Stubbs, Amherst, MA (US); Todd Emrick, South Deerfield, MA (US)

(73) Assignee: University of Massachusetts, Boston, MA (US)

( * ) Notice: Subject to any disclaimer, the term of this patent is extended or adjusted under 35 U.S.C. 154(b) by 250 days.

(21) Appl. No.: 16/415,081

(22) Filed: May 17, 2019

(65) Prior Publication Data

US 2019/0352249 A1 Nov. 21, 2019

Related U.S. Application Data

(60) Provisional application No. 62/673,010, filed on May 17, 2018.

(51) Int. Cl.
| | |
|---|---|
| *C07C 65/40* | (2006.01) |
| *C08G 63/06* | (2006.01) |
| *C08L 67/04* | (2006.01) |
| *C07C 51/347* | (2006.01) |

(52) U.S. Cl.
CPC .............. *C07C 65/40* (2013.01); *C08G 63/06* (2013.01); *C08L 67/04* (2013.01); *C07C 51/347* (2013.01); *C08L 2201/02* (2013.01)

(58) Field of Classification Search
CPC ....... C07C 65/40; C07C 51/347; C07C 69/94; C08G 63/06; C08G 63/065; C08L 67/04; C08L 2201/02
See application file for complete search history.

(56) References Cited

PUBLICATIONS

Ranganathan et al.; Polymer Degradation and Stability, 2008, vol. 93, p. 1059-1066.*
Emrick et al.; Journal of Materials Chemistry, 2010, vol. 20, p. 3681-3687.*
Mir et al.; Polymer, 2016, vol. 84, p. 59-64.*
Choudhary et al.; Macromolecules, 2017, p. 3772-3778.*
Ravichandran, S.; Sustainable Routes to Conjugated Polymers and Non-Halogenated Flame Retardants, 2012, p. i-178.*
Ellzey, K.A.; Fire-Resistant Polymers Containing Bisphenol C and Deoxybenzoin Derivatives, 2014, p. i-134.*

* cited by examiner

*Primary Examiner* — Robert S Jones, Jr.
(74) *Attorney, Agent, or Firm* — Milstein Zhang & Wu LLC

(57) ABSTRACT

The invention provides novel deoxybenzoin-containing polymers exhibiting branched (including hyperbranched) architectures, and related methods and uses thereof.

20 Claims, 14 Drawing Sheets

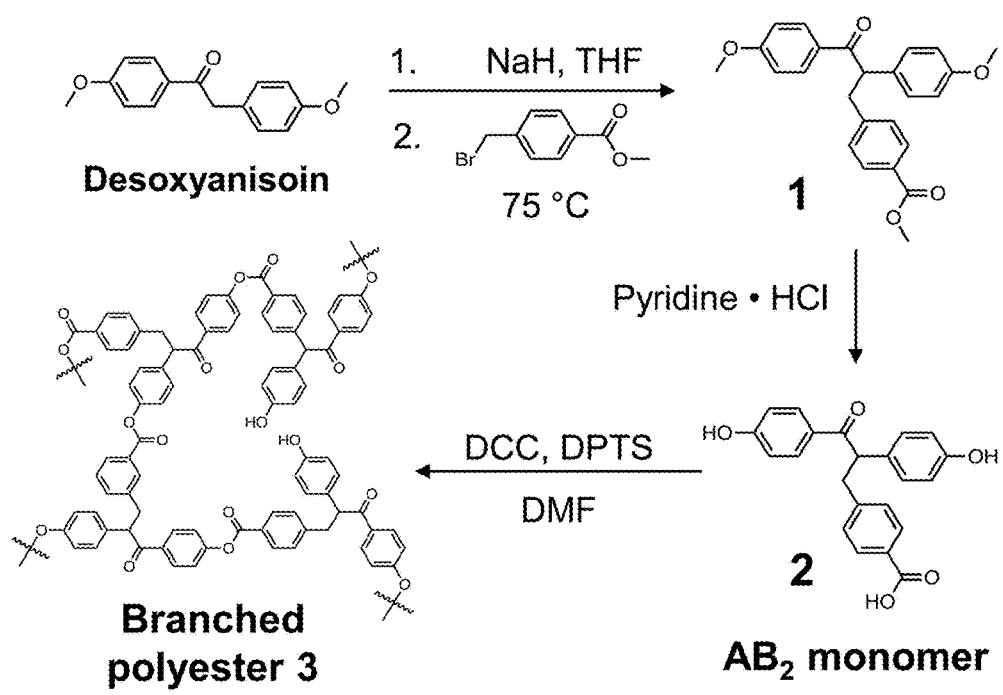
FIG. 1. Benzylation of desoxyanisoin with methyl 4-(bromomethyl)benzoate, followed by demethylation to afford $AB_2$ monomer 2 for carbodiimide-catalyzed polyester formation.

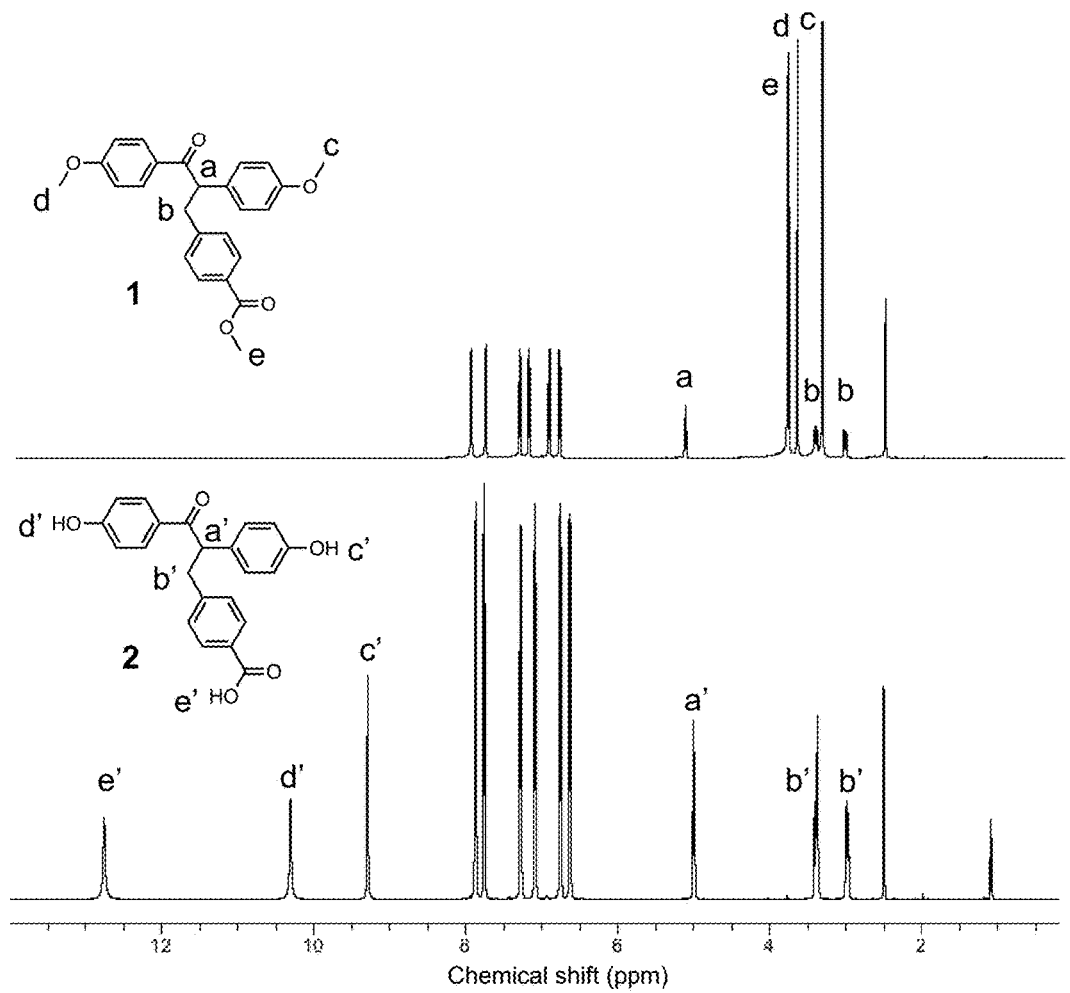
FIG. 2. $^1$H NMR spectra of compounds 1 and 2 in DMSO-$d_6$.

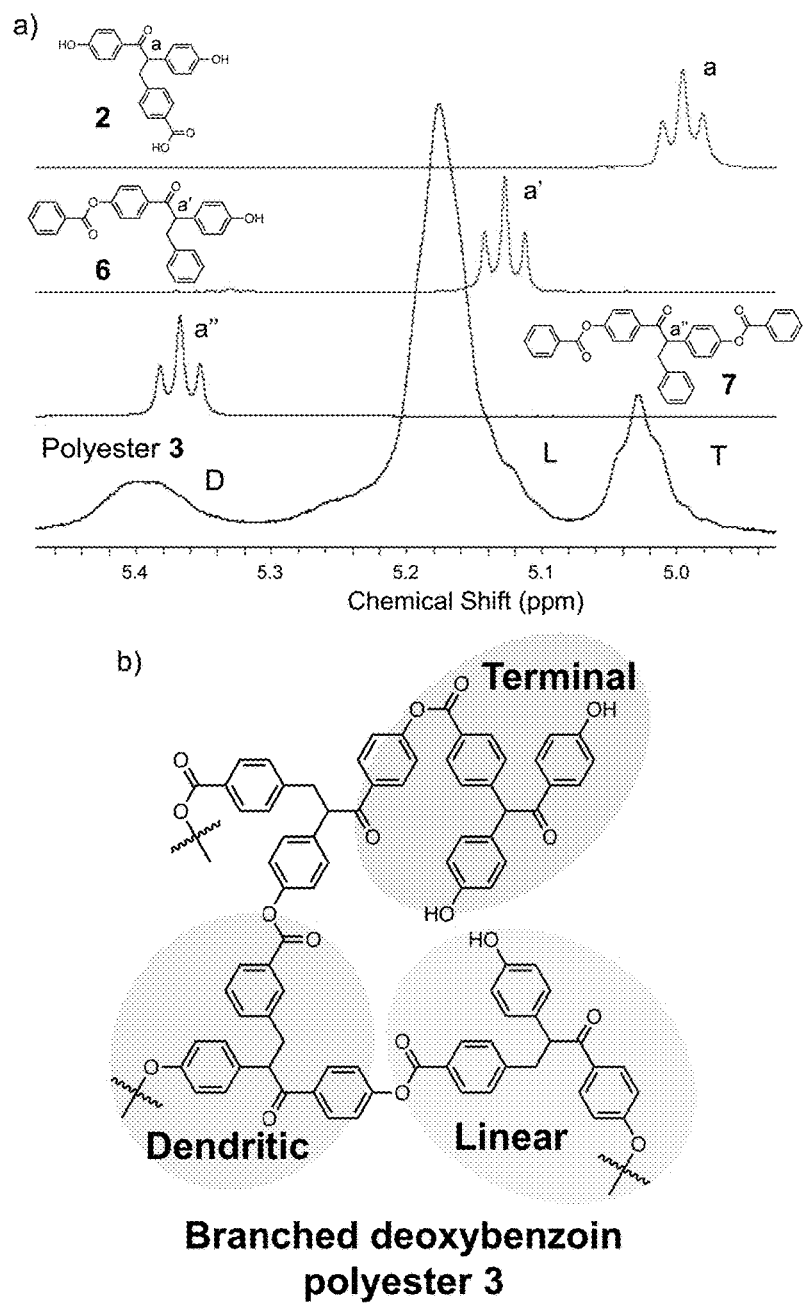
FIG. 3. (a) $^1$H NMR of AB$_2$ monomer 2, linear unit small molecule analog 6, dendritic unit small molecule analog 7, and branched polyester 3. b) Structure of branched deoxybenzoin polyester 3.

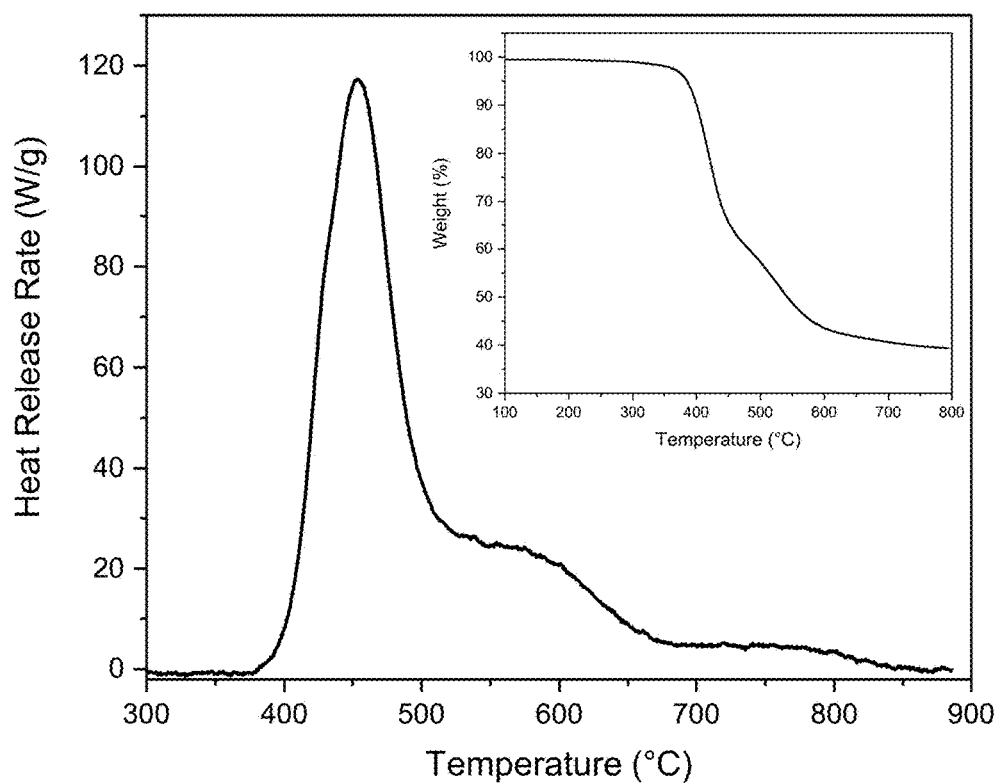
FIG. 4. Representative heat release curve of branched deoxybenzoin polyester obtained by microscale combustion calorimetry. Inset: TGA of branched deoxybenzoin polyester exhibiting char residue of 40% at 750 °C.

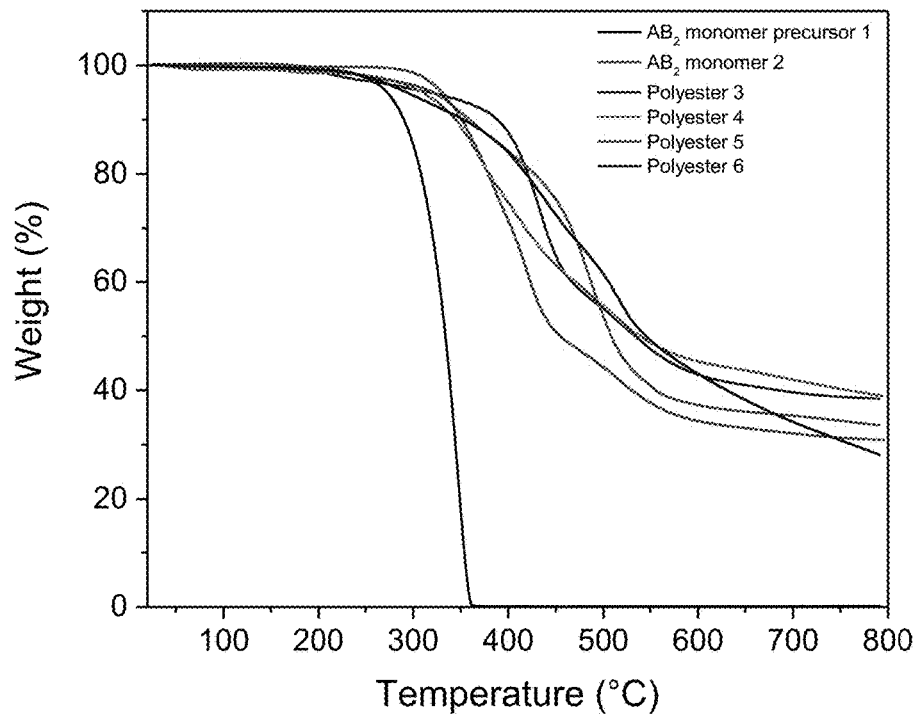
FIG. 5. Left: TGA thermograms of $AB_2$ monomer precursor 1, $AB_2$ monomer 2, and polyesters 3-6. TGA was conducted under a $N_2$ atmosphere.
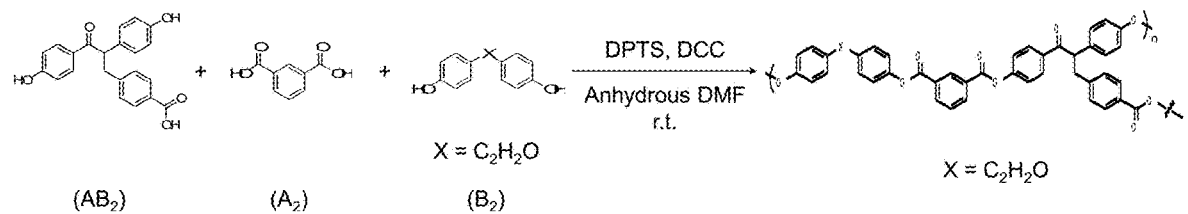
FIG. 6. $AB_2$ monomer integrated into $A_2$ and $B_2$ polymerizations by carbodiimide-catalyzed esterification.

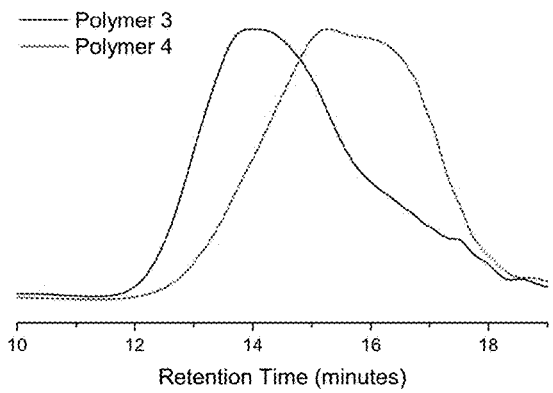
FIG. 7. GPC traces of deoxybenzoin-containing branched polyesters in DMF as the eluting solvent.
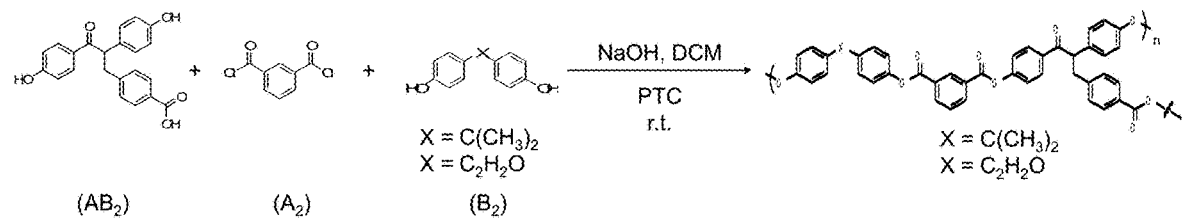
FIG. 8. Deoxybenzoin AB$_2$ monomer integrated into A$_2$ and B$_2$ polymerizations by interfacial polymerization.

(a)
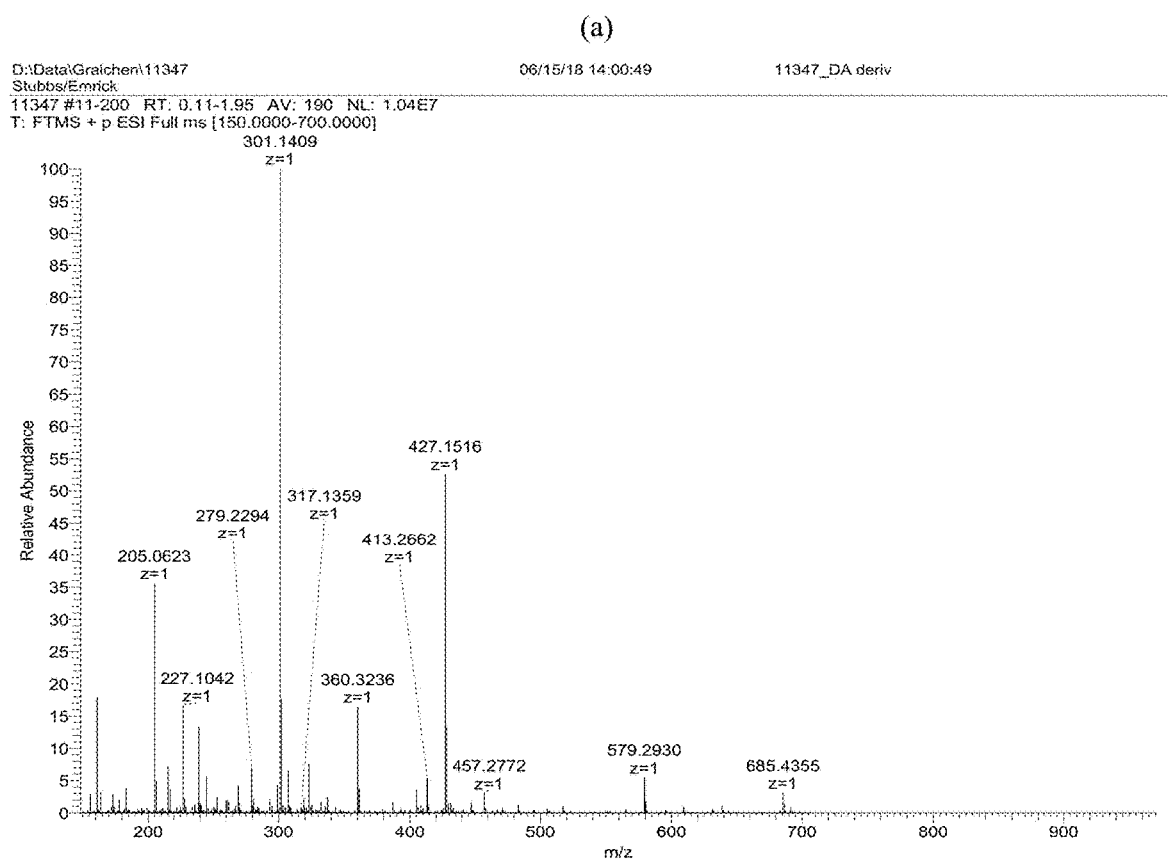
FIG. 9. HRMS-ESI of compound 1 (a) and AB$_2$ monomer 2 (b) exhibiting molecular weights of 427.1516 and 385.1046 a.m.u., respectively.

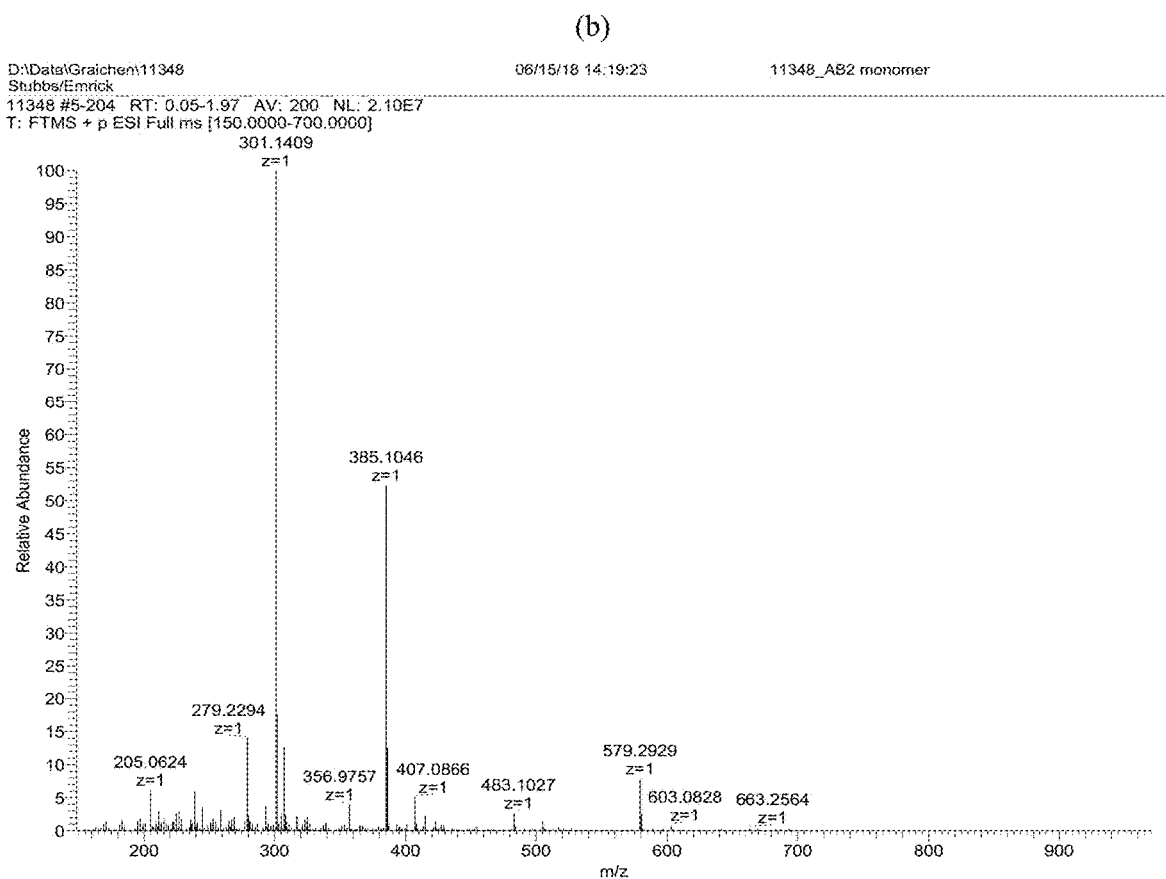
FIG. 9 (Cont'd). HRMS-ESI of compound 1 (a) and $AB_2$ monomer 2 (b) exhibiting molecular weights of 427.1516 and 385.1046 a.m.u., respectively.

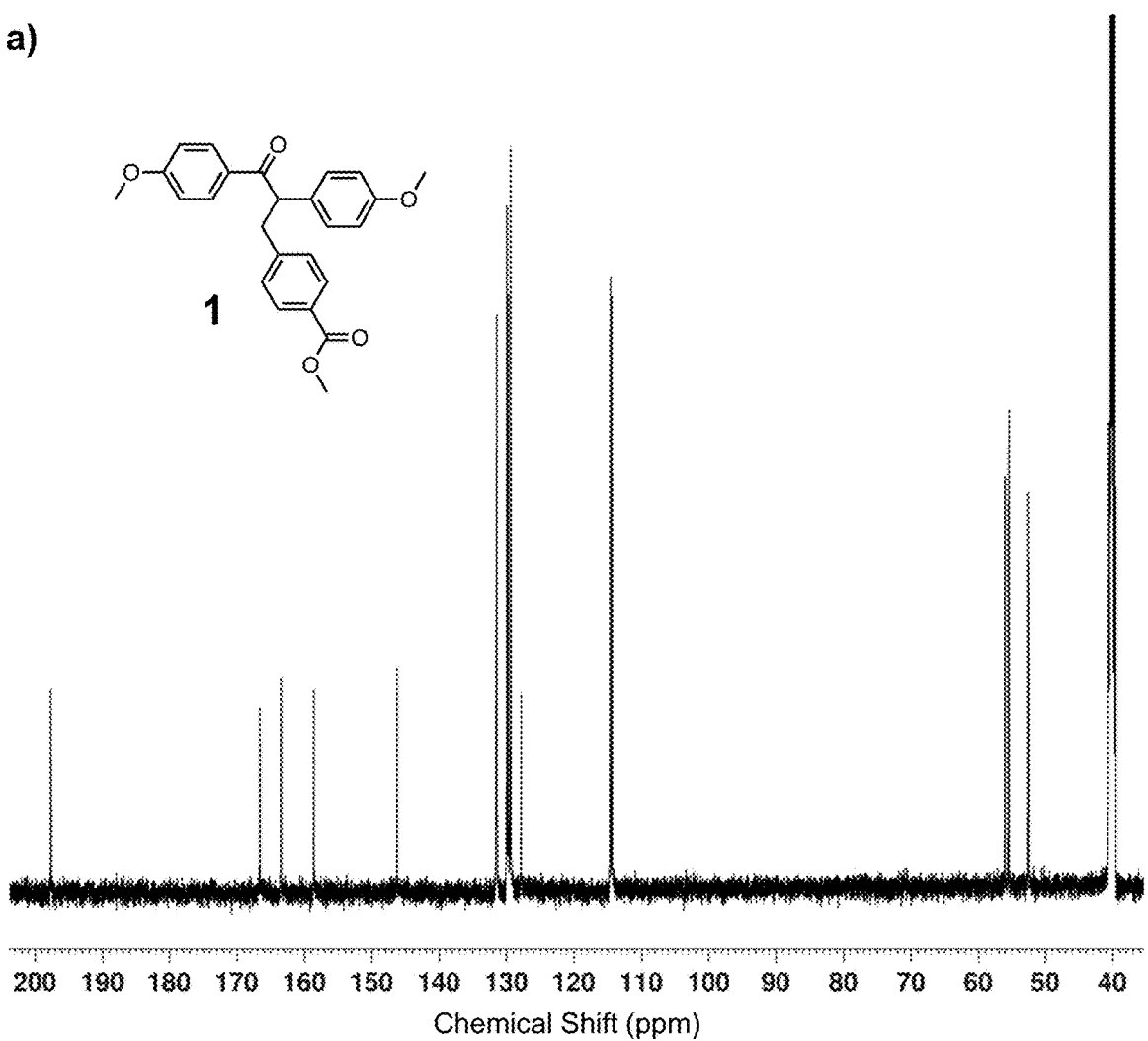
FIG. 10. $^{13}$C NMR spectra of compound 1 (a) and AB$_2$ monomer 2 (b) in DMSO-$d_6$.

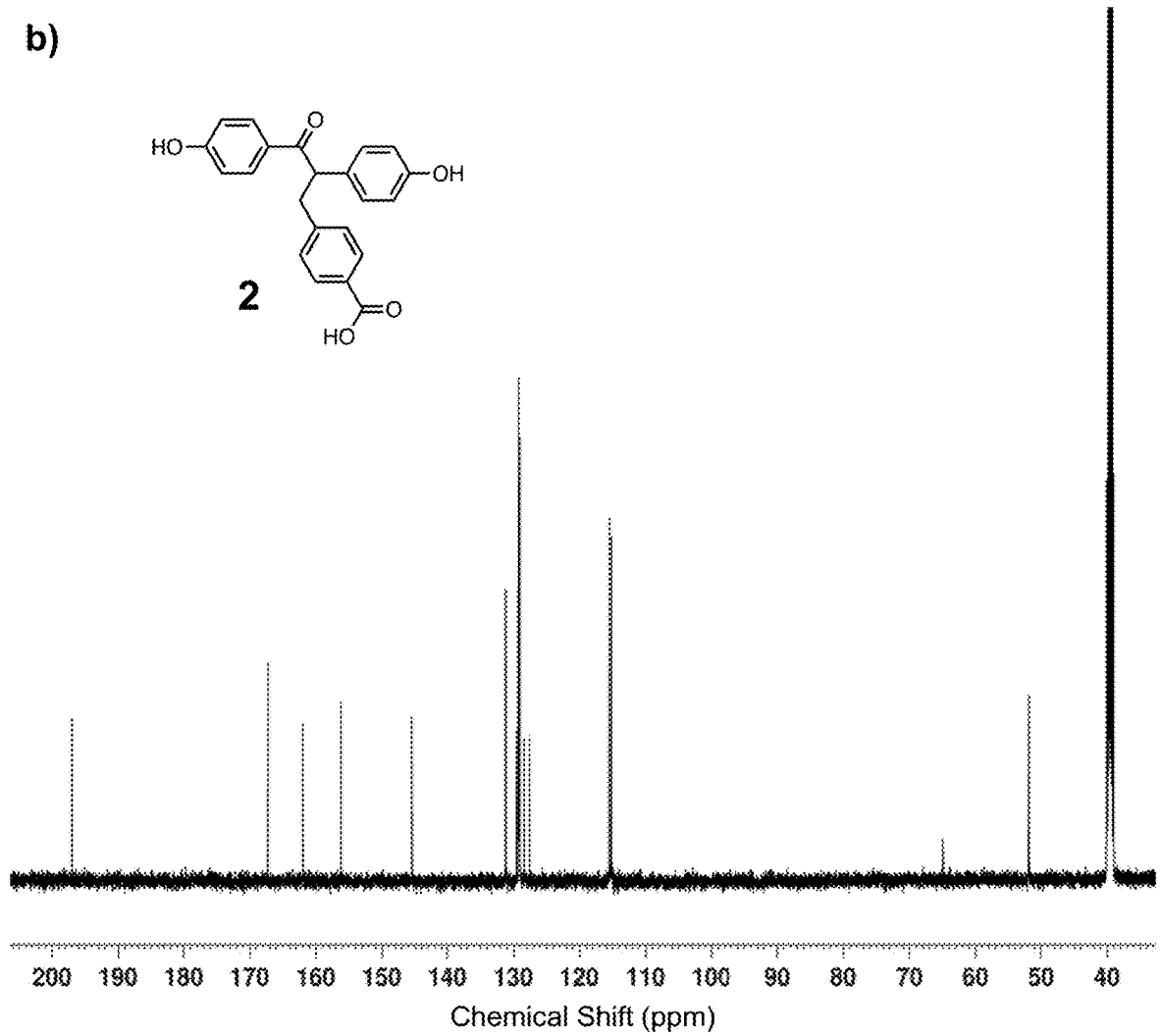
FIG. 10 (Comt'd). $^{13}$C NMR spectra of compound 1 (a) and AB$_2$ monomer 2 (b) in DMSO-$d_6$.

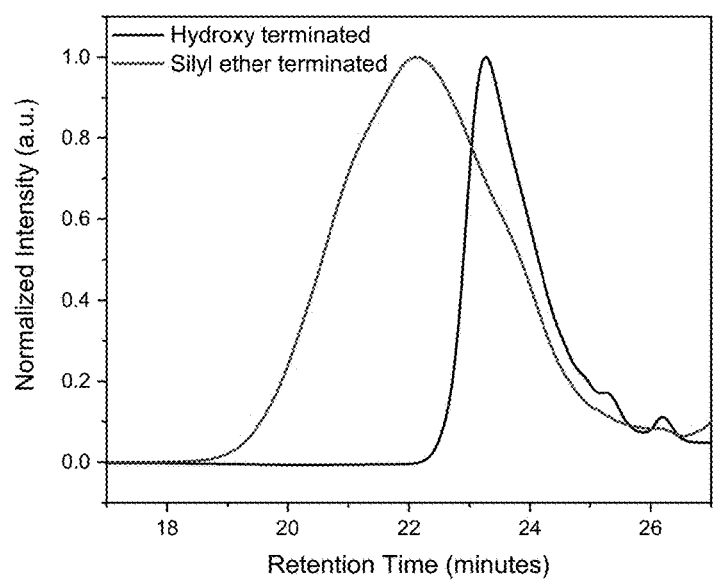
FIG. 11. GPC (THF eluent) of hydroxy-terminated branched deoxybenzoin polyester 3 and silyl-ether shielded polyester 3.

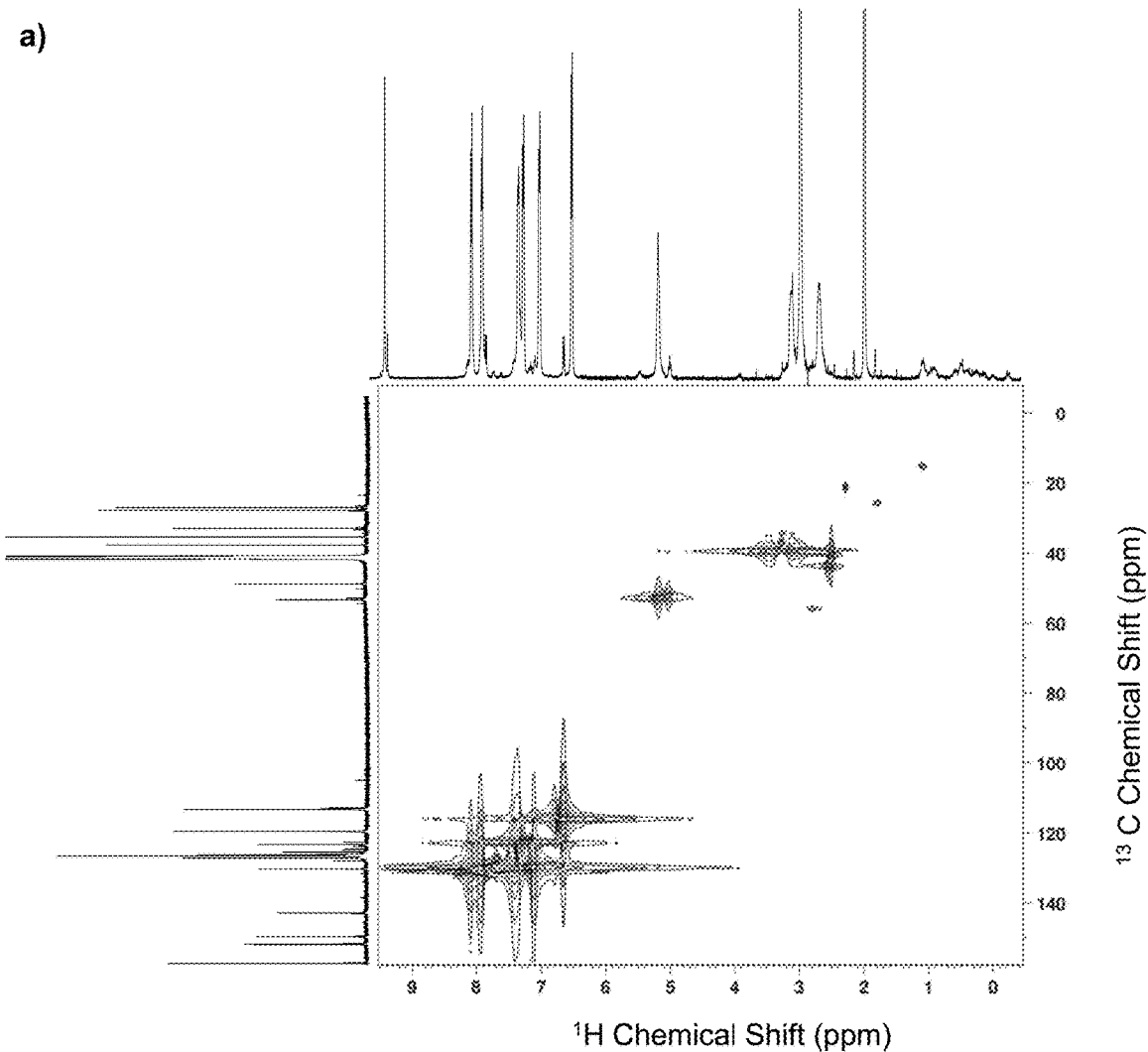
FIG. 12. (a): 2D heteronuclear multiple quantum correlation (HMQC) between $^1$H and $^{13}$C nuclei of branched deoxybenzoin polyester 3 in DMSO-$d_6$. (b): Shows the correlation between the dendritic, linear, and terminal units of the branched polyester.

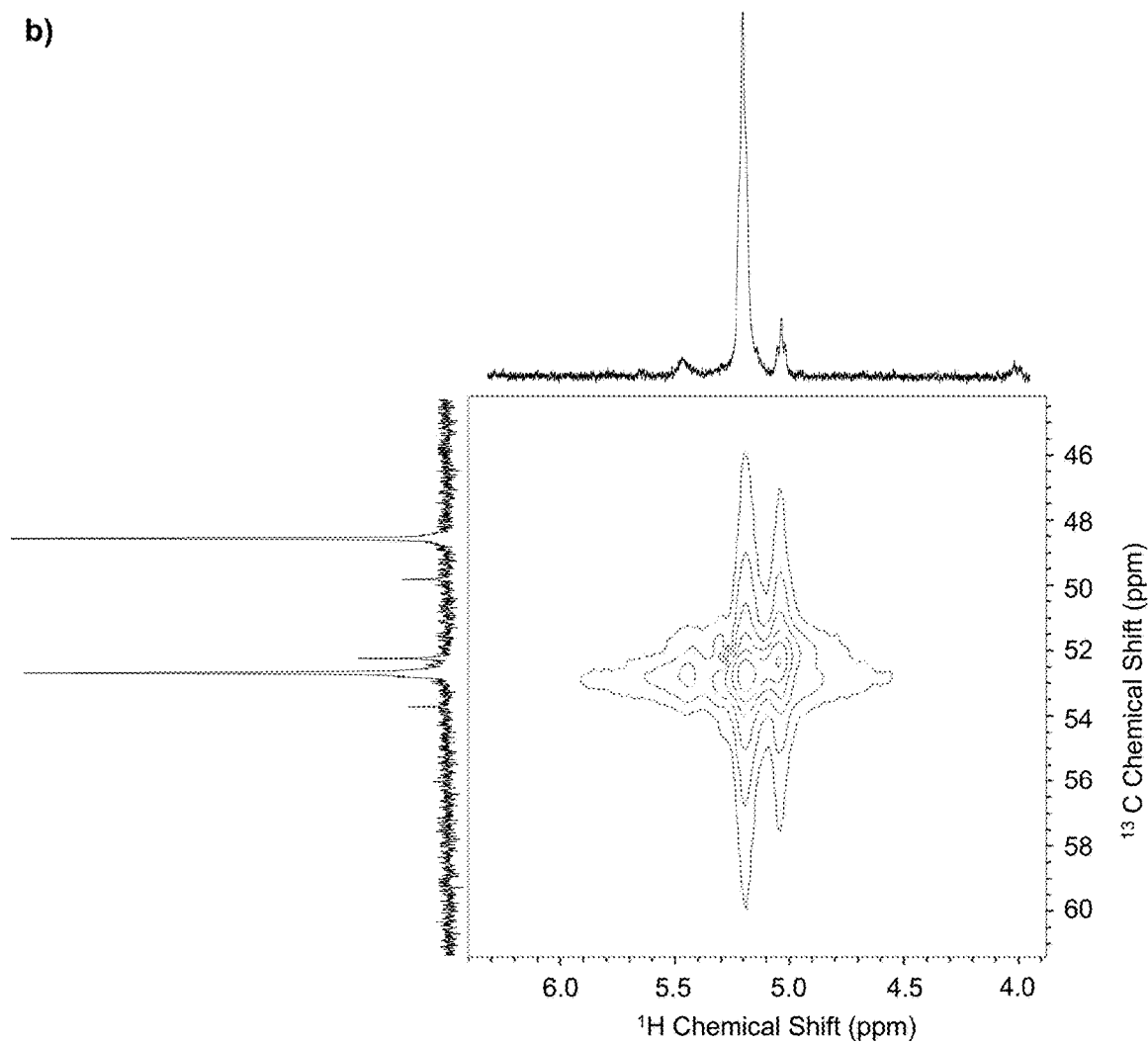
FIG. 12 (Cont'd). (a): 2D heteronuclear multiple quantum correlation (HMQC) between $^1$H and $^{13}$C nuclei of branched deoxybenzoin polyester 3 in DMSO-$d_6$. (b): Shows the correlation between the dendritic, linear, and terminal units of the branched polyester.

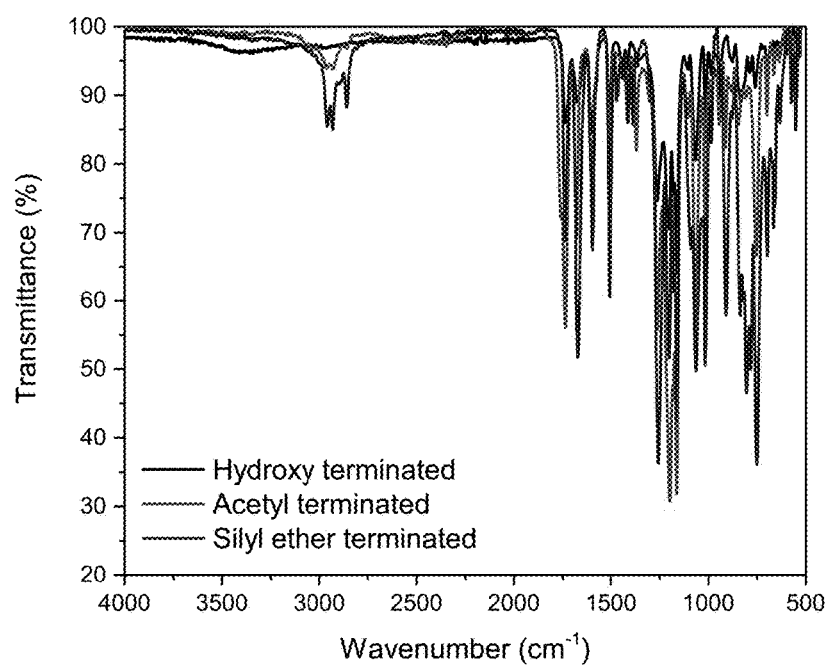
FIG. 13. ATR-FTIR of hydroxyl, acetyl, and silyl ether chain-end modified branched deoxybenzoin polyester 3.

DEOXYBENZOIN MONOMERS AND BRANCHED POLYMERS PREPARED THEREFROM

PRIORITY CLAIMS AND RELATED PATENT APPLICATIONS

This application claims the benefit of priority to U.S. Provisional Application Ser. No. 62/673,010, filed on May 17, 2018, the entire content of which is incorporated herein by reference in its entirety.

STATEMENT REGARDING FEDERALLY FUNDED RESEARCH OR DEVELOPMENT

This invention was made with government support under Grant No. 17-G-012 awarded by the Federal Aviation Administration. The Government has certain rights in the invention.

TECHNICAL FIELD OF THE INVENTION

The invention relates to flame retardant polymers. More particularly, the invention relates to deoxybenzoin-containing polymers exhibiting branched (including hyperbranched) architectures, and related methods and uses thereof.

BACKGROUND OF THE INVENTION

Polymers are a mainstay of modern society are used extensively in textiles, upholstery, construction materials, vehicles, and microelectronics. The inherent flammability of many polymers poses a significant threat, especially in enclosed or isolated spaces. This extensive use of polymers in plastics, rubbers, and textiles has been recognized as a flammability hazard and remains an important challenge in polymer research.

Currently, flame retardant additives containing halogens or inorganic compounds are integrated into polymers to counteract their flammability. Halogenated flame retardants act as radical scavengers during gas phase combustion to decrease the overall heat release of the polymer. (Green 19961 *Fire Sci.* 14, 426; Camino, et al. 1991 *Polym. Degrad. Stab.* 33, 131; Dasari, et al. 2013 *Prog. Polym. Sci.* 38, 1357; Altarawneh, et al. 2019 *Prog. Energy Combust. Sci.* 70, 212.)

Despite their effectiveness, many halogenated flame retardants face scrutiny due to health concerns associated with their production, use, and environmental accumulation. On the other hand, non-halogenated, inorganic flame retardants typically function by thermally induced formation of a solid phase barrier that slows combustion of the underlying polymer fuel. These inorganic compounds are less problematic than halogens with respect to toxicity, but to be effective require high weight percent loadings, which may negatively impact the mechanical properties of the materials into which they are integrated. (Dasari, et al. 2013 *Prog. Polym. Sci.* 38, 1357; Laoutid, et al. 2009 *Mat. Sci. Eng. R* 63, 100; Letcher, et al. 2018 *Sci. Total Environ.* 610, 121; Noyes, et al. 2015 *Tox. Sci.* 145, 177; Stapleton, et al. 2011 *Environ. Sci. Tech.* 45, 5323; Lu, et al. 2018 *Compos. Part A Appl. Sci. Manuf.* 113, 1.)

In recent years, polymers containing deoxybenzoin moieties have emerged as effective flame retardants, both as stand-alone materials and in blends with commodity polymers. For example, previously reported deoxybenzoin-containing polyesters exhibited high char yields (as high as 42%) by thermogravimetric analysis (TGA) and low heat release capacities <100 J g$^{-1}$ K$^{-1}$, as determined by microscale combustion calorimetry (MCC). MCC, an oxygen consumption technique, allows milligram-scale testing of materials, and produces data that corresponds closely to heat release capacity (HRC) and total heat release rate (THR) values derived from larger-scale methods (hundreds of grams), such as the UL-94 test and cone calorimetry. (Hu, et al. 2017 *J. Appl. Polym. Sci.* 134, 1; Zhang, et al. 2015 *RSC Adv.* 5, 87609; Ellzey, et al. 2006 *Marcomolecules* 39, 3553; Lyon, et al. 2007 *J. Therm. Anal. Cal.* 89, 441; Lyon, et al. 2009 *Polymer* 50, 2608; Lyon, et al. 2004 *J. Anal. Appl. Pyrolysis* 71, 27; Cogen, et al. 2009 *Fire Mater.* 33, 33; Guo, et al. 2018 *J. Test. Eval.* 46, 1090; Filipczak, et al. 2005 *Fire Saf. J.* 40, 628.)

Following landmark reports on hyperbranched aromatic polymer syntheses from AB$_2$ monomers by Kim and Webster, numerous researchers have advanced this field to the benefit of polymer chemistry and materials processing. Prominent examples include the work of Fréchet on the polymerization of AB$_x$ (x≥2) and A$_2$+B$_3$ monomers to afford hyperbranched structures, Wooley on the synthesis of hyperbranched aromatic polyesters from AB$_2$ monomers, and Hult on a one-step approach to aliphatic hyperbranched polyesters. Common to hyperbranched polymers is a significantly improved solubility and processability relative to linear versions, and a great degree of chemical versatility owing to the abundance of reactive chain-ends that are a consequence of branching. (Kim, et al. 1992 *Macromolecules* 25, 5561; Uhrich, et al. 1992 *Macromolecules* 25, 4583; Emrick, et al. 1999 *Macromolecules* 32, 6380; Hawker, et al. 1991 *J. Am. Chem. Soc.* 113, 4583; Wooley, et al. 1994 *Polym. J.* 26, 187; Malmström, et al. 1995 *Macromolecules* 28, 1698; Malmström et al. 1996 *Macromolecules* 29, 1222.)

There is a pressing need to effectively couple polymer chemistry and architecture towards materials that minimize heat release and for novel synthetic strategies toward a broad range of structurally and functionally diverse flame-retardant polymers.

SUMMARY OF THE INVENTION

The invention provides a novel platform of low flammability polymer materials. In particular, the invention provides deoxybenzoin-containing monomers that generate branched or hyperbranched polymer architectures. The materials and the chemistry disclosed herein afford new and improved flame-retardant materials and additives. For example, facile integration of deoxybenzoin-containing polymers into processing techniques, such as additives to linear polymers, can simultaneously lower melt viscosity and improving flame-resistance of conventional polymers.

For example, one-pot syntheses of highly branched or "hyperbranched" polymers with distinct physical and chemical properties are disclosed herein. Synthesis of a deoxybenzoin-containing AB$_2$ monomer and its use in step-growth polymerization to prepare branched aromatic polyesters were thoroughly studied. Highly soluble deoxybenzoin polymers were obtained with degrees of branching reaching 0.36 and estimated molecular weights approaching 20 kDa. The phenolic chain-ends of the polymer allowed for post-polymerization modification by silylation and esterification chemistry. Thermogravimetric analysis (TGA) and microscale combustion calorimetry (MCC) revealed these novel aromatic polyesters to possess the critically important characteristics of flame-retardant polymers, such as high char yield, and low heat release.

In one aspect, the invention generally relates to a compound having the structural formula of:

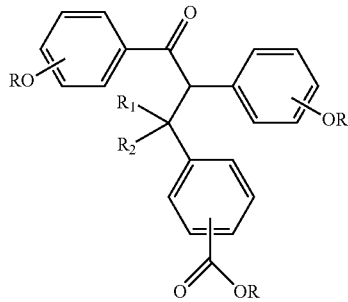

wherein each of R, $R_1$ and $R_2$ is independently selected from H and ($C_1$-$C_6$) alkyl groups.

In another aspect, the invention generally relates to a polymer prepared from a compound having the structural formula of:

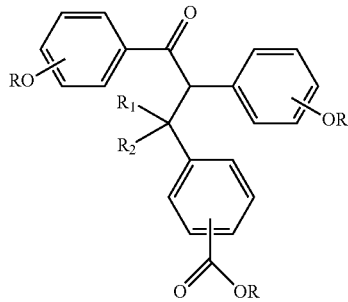

wherein each of R, $R_1$ and $R_2$ is independently selected from H and ($C_1$-$C_6$) alkyl groups.

In yet another aspect, the invention generally relates to a polymer comprising a structural unit of the formula:

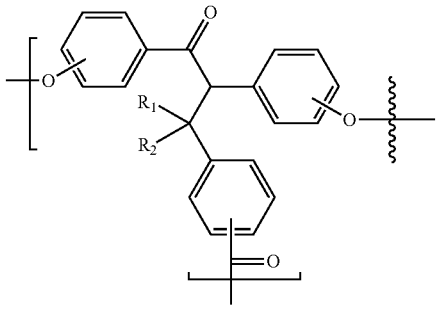

wherein each of $R_1$ and $R_2$ is independently selected from H and ($C_1$-$C_6$) alkyl groups.

In yet another aspect, the invention generally relates to a resin composition comprising a polymer disclosed herein.

In yet another aspect, the invention generally relates to a flame retardant additive comprising a polymer disclosed herein.

In yet another aspect, the invention generally relates to a material comprising the flame retardant disclosed herein.

In yet another aspect, the invention generally relates to a minimal- or non-flammable material comprising a polymer disclosed herein.

BRIEF DESCRIPTION OF THE DRAWINGS

FIG. 1. Benzylation of desoxyanisoin with methyl 4-(bromomethyl)benzoate, followed by demethylation to afford $AB_2$ monomer 2 for carbodiimide-catalyzed polyester formation.

FIG. 2. $^1$H NMR spectra of compounds 1 and 2 in DMSO-$d_6$.

FIG. 3. (a) $^1$H NMR of $AB_2$ monomer 2, linear unit small molecule analog 6, dendritic unit small molecule analog 7, and branched polyester 3. b) Structure of branched deoxybenzoin polyester 3.

FIG. 4. Representative heat release curve of branched deoxybenzoin polyester obtained by microscale combustion calorimetry. Inset: TGA of branched deoxybenzoin polyester exhibiting char residue of 40% at 750° C.

FIG. 5. Left: TGA thermograms of $AB_2$ monomer precursor 1, $AB_2$ monomer 2, and polyesters 3-6. TGA was conducted under a $N_2$ atmosphere.

FIG. 6. $AB_2$ monomer integrated into $A_2$ and $B_2$ polymerizations by carbodiimide-catalyzed esterification.

FIG. 7. GPC traces of deoxybenzoin-containing branched polyesters in DMF as the eluting solvent.

FIG. 8. Deoxybenzoin $AB_2$ monomer integrated into $A_2$ and $B_2$ polymerizations by interfacial polymerization.

FIG. 9. HRMS-ESI of compound 1 (a) and $AB_2$ monomer 2 (b) exhibiting molecular weights of 427.1516 and 385.1046 a.m.u., respectively.

FIG. 10. $^{13}$C NMR spectra of compound 1 (a) and $AB_2$ monomer 2 (b) in DMSO-$d_6$.

FIG. 11. GPC (THF eluent) of hydroxy-terminated branched deoxybenzoin polyester 3 and silyl-ether shielded polyester 3.

FIG. 12. (a): 2D heteronuclear multiple quantum correlation (HMQC) between $^1$H and $^{13}$C nuclei of branched deoxybenzoin polyester 3 in DMSO-$d_6$. (b): Shows the correlation between the dendritic, linear, and terminal units of the branched polyester.

FIG. 13. ATR-FTIR of hydroxyl, acetyl, and silyl ether chain-end modified branched deoxybenzoin polyester 3.

DETAILED DESCRIPTION OF THE INVENTION

The invention provides novel deoxybenzoin-containing monomers that generate non-halogenated branched or hyperbranched hydrocarbon polymers that are inherently flame retardant. The branched polymers described herein exhibit impressively low heat release properties. A new $AB_2$ monomer is designed and synthesized that affords aromatic branched polymers by carbodiimide-catalyzed esterification as the polymerization mechanism (FIG. 1). While many deoxybenzoin-based polymers exhibit exceptionally low flammability, in some cases the predominately linear polymer architecture produces materials with relatively low solubility. As disclosed herein, these deoxybenzoin-based polymers proved easy to prepare and have appreciably greater solubility than prior linear versions, allowing access to higher molecular weight polymers with easier processability.

In addition, a facile, one-pot preparation of branched deoxybenzoin-containing polymers by carbodiimide-catalyzed polyesterification is disclosed. The synthesized polyesters exhibit appreciable molecular weights and significant degrees of branching with opportunities for post-polymerization modification. The deoxybenzoin branched polyesters exhibit high solubility while maintaining low heat release properties and high char yields as compared to the linear versions.

The materials and the chemistry disclosed herein afford a novel platform for minimal- or non-flammable materials and additives. Importantly, these hydrocarbons possess suitable processability as well as performance characteristics. The compounds and methods disclosed herein allow facile integration of deoxybenzoin-containing polymers into processing techniques. The branched or hyperbranched polymer architectures impart lower melt viscosity and significantly improved flame-resistance. The heat release and char yield properties from these novel compounds were realized without the presence of conventional anti-flammable additives such as halogenated organic molecules or phosphorous-containing structures.

In one aspect, the invention generally relates to a compound having the structural formula of:

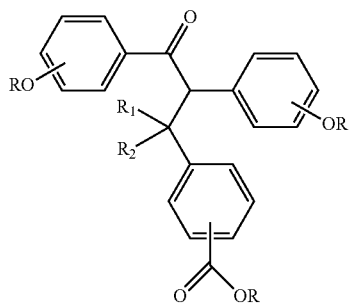

wherein each of R, $R_1$ and $R_2$ is independently selected from H and ($C_1$-$C_6$) alkyl groups.

In certain embodiments, each R is an alkyl, e.g., a ($C_1$, $C_2$, $C_3$, $C_4$, $C_5$, or $C_6$) alkyl group.

In certain embodiments, each R is a methyl.

In certain embodiments, each R is H.

In certain embodiments, at least one of $R_1$ and $R_2$ is H.

In certain embodiments, each of $R_1$ and $R_2$ is H.

In certain embodiments, at least one of $R_1$ and $R_2$ is a ($C_1$, $C_2$, $C_3$, $C_4$, $C_5$, or $C_6$) alkyl group.

In certain embodiments, each of $R_1$ and $R_2$ is a ($C_1$, $C_2$, $C_3$, $C_4$, $C_5$, or $C_6$) alkyl group.

In certain embodiments, the compound has the following structural formula:

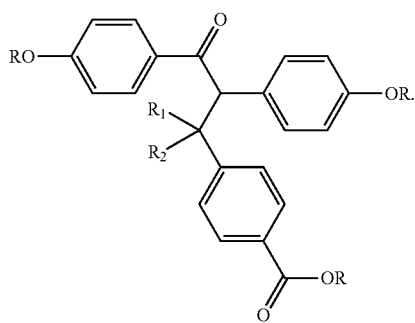

In another aspect, the invention generally relates to a polymer prepared from a compound having the structural formula of:

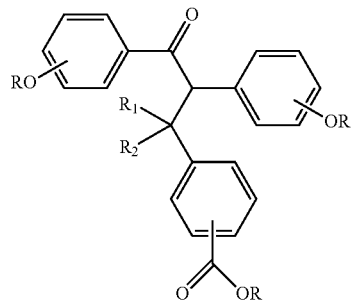

wherein each of R, $R_1$ and $R_2$ is independently selected from H and ($C_1$-$C_6$) alkyl groups.

In certain embodiments of the polymer, each R is an alkyl, e.g., a ($C_1$, $C_2$, $C_3$, $C_4$, $C_5$, or $C_6$) alkyl group.

In certain embodiments of the polymer, each R is a methyl.

In certain embodiments of the polymer, each R is H.

In certain embodiments of the polymer, at least one of $R_1$ and $R_2$ is H.

In certain embodiments of the polymer, each of $R_1$ and $R_2$ is H.

In certain embodiments of the polymer, at least one of $R_1$ and $R_2$ is a ($C_1$, $C_2$, $C_3$, $C_4$, $C_5$, or $C_6$) alkyl group.

In certain embodiments of the polymer, each of $R_1$ and $R_2$ is a ($C_1$, $C_2$, $C_3$, $C_4$, $C_5$, or $C_6$) alkyl group.

In certain embodiments of the polymer, the compound has the following structural formula:

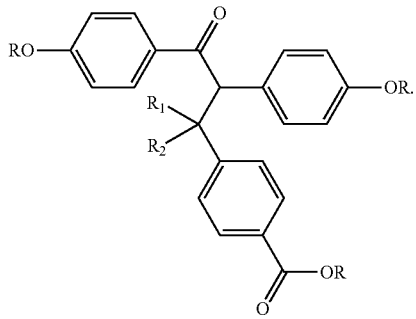

In yet another aspect, the invention generally relates to a polymer comprising a structural unit of the formula:

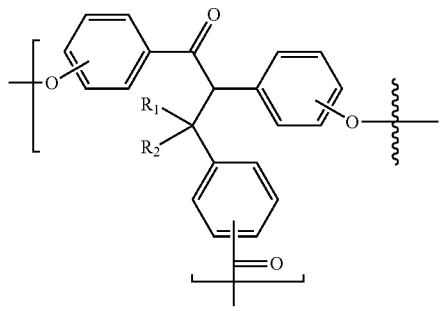

wherein each of $R_1$ and $R_2$ is independently selected from H and ($C_1$-$C_6$) alkyl groups.

In certain embodiments of the polymer, at least one of $R_1$ and $R_2$ is H.

In certain embodiments of the polymer, each of $R_1$ and $R_2$ is H.

In certain embodiments of the polymer, at least one of $R_1$ and $R_2$ is a ($C_1$, $C_2$, $C_3$, $C_4$, $C_5$, or $C_6$) alkyl group.

In certain embodiments of the polymer, each of $R_1$ and $R_2$ is a ($C_1$, $C_2$, $C_3$, $C_4$, $C_5$, or $C_6$) alkyl group.

In certain embodiments of the polymer, the structural unit is:

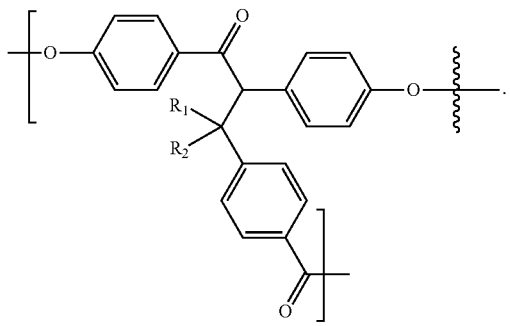

In certain embodiments, the polymer is a homopolymer.

In certain embodiments, the polymer is a copolymer.

The polymers of the invention may have molecular weight suitable for a range of materials applications. In certain embodiments, the polymers have a molecular weight $M_w$, from about 1,000 to about 100,000 g/mole (e.g., from about 1,000 to about 50,000, from about 1,000 to about 20,000, from about 5,000 to about 100,000, from about 10,000 to about 100,000, from about 5,000 to about 50,000, from about 10,000 to about 30,000 g/mole).

In yet another aspect, the invention generally relates to a resin composition comprising a polymer disclosed herein.

In yet another aspect, the invention generally relates to a flame retardant additive comprising a polymer disclosed herein.

In yet another aspect, the invention generally relates to a material comprising the flame retardant disclosed herein.

In yet another aspect, the invention generally relates to a minimal- or non-flammable material comprising a polymer disclosed herein.

EXAMPLES

Polymer Synthesis and Characterization

Monomer 2 was synthesized as illustrated in FIG. 1 and polymerized to obtain branched, deoxybenzoin-containing polyesters. The monomer was prepared by deprotonating the methylene group of desoxyanisoin with sodium hydride, followed by nucleophilic substitution onto methyl 4-(bromomethyl)benzoate, affording compound 1 as a white powder in 86% yield. Reaction of 1 with pyridine hydrochloride removed all three methyl groups to afford benzoic acid-substituted bis-hydroxydeoxybenzoin 2 as a white powder in 76% yield after purification. High resolution mass spectroscopy-electrospray ionization (HRMS-ESI) analysis confirmed the expected molecular weights of 1 and 2 as 427.1516 and 385.1046 a.m.u., respectively (FIG. 9).

The $^1$H NMR spectrum of 2, shown in FIG. 2, indicated complete demethylation of 1 by disappearance of its methyl ester (3.80 ppm) and methyl ether (3.77 and 3.66 ppm) proton signals, and appearance of new signals for the benzoic acid (12.76 ppm) and phenolic protons (10.31 and 9.29 ppm). $^{13}$C NMR spectroscopy of 2 showed loss of the methyl peaks originally present at 51.91, 54.90, and 55.45 ppm in compound 1 (FIG. 10). AB$_2$ monomer 2 was then polymerized by carbodiimide coupling, using EDC and DMAP/p-TSA (DPTS) in anhydrous DMF according to literature. After five minutes, the transparent solution turned opaque. The mixture was allowed to stir at 23° C. under nitrogen atmosphere for 12-72 hours. The resultant viscous mixture was filtered and precipitated into methanol to afford a white powder in ~80% yield.

The estimated molecular weights of branched polymers, relative to linear standards, are often lower than that of the actual molecular weight due to their smaller hydrodynamic radii that is a consequence of branching. In addition, the abundance of chain-ends in highly branched polymers may lead to interactions with the stationary phase employed in chromatographic analysis. (Malmström, et al. 1997 Rev. Macromol. Chem. Phys. 37, 205.) A representative GPC analysis of polyester 3, (eluting in THF and using linear PS calibration standards) gave $M_n$ and $M_w$ values of 4.9 and 6.3 kDa, whereas the OTMS-protected version (converting —OH to —OTMS with HMDS) led to structures with estimated $M_n$ of 11 kDa and $M_w$ of 20 kDa (FIG. 11). This greater than doubling of molecular weight of the silylated polymers (i.e., more rapid GPC elution) indicates that the unprotected polymer might engage in undesirable stationary phase interactions that artificially underestimates molecular weight. Notably, for the same OTMS-protected sample, GPC equipped with a multi-angle laser light scattering detector (eluting in THF with 0.1 vol. % trimethylamine), gave an $M_w$ of 17 kDa, confirming the appreciable molecular weights of the structures obtained in this esterification polymerization. The molecular weights of the branched polyesters were several times larger than previously reported linear deoxybenzoin polyarylates, owing to the branched architecture overcoming solubility limitations encountered with the linear versions.

The $^1$H NMR spectrum of polyester 3 exhibited three signals in the 5.00-5.40 ppm range, which we assign to methine protons of dendritic (5.39 ppm), linear (5.18 ppm), and terminal (5.03 ppm) units of the polymer. These same methine signals in the $^{13}$C NMR spectrum appeared at 52.9 (dendritic), 52.6 (linear), and 52.2 (terminal) ppm. To support these assignments, small molecule analogs were prepared by substituting deoxybenzoin with benzyl bromide followed by demethylation to afford compound 5, which was converted to the corresponding phenyl esters shown as 6 and 7 in FIG. 3. $^1$H NMR spectroscopy of 7 revealed the methine proton to shift from 5.00 ppm (a) in 2 to 5.37 ppm (a"). Similarly, a downfield shift of the methine proton from 5.00 ppm (a) to 5.42 ppm (D) was observed upon polymerization of 2, attributed to the dendritic unit. Interestingly, esterification of 5 revealed the phenol nearest the ketone to react fully in <1 hour, whereas reaction of the other phenol was incomplete even after 24 hours. Such inequivalent reactivity departs from ideal polymerization conditions and, as discussed later, would be expected to reduce the degree of branching (DB) of the polymer products.

As another control experiment, mono-substituted benzoate ester 6 was prepared by reacting compound 5 with one equivalent of benzoic acid. The methine proton of 6 appeared at 5.12 ppm (a'), expectedly close to that of the assigned linear unit of the polymer at 5.17 ppm (L). Finally, the methine proton in the terminal unit, which contains two unreacted phenols, appears at 5.02 ppm (T). 2D heteronuclear multiple quantum correlation (HMQC) experiments, which correlates protons with directly bonded heteronuclei, revealed the $^{13}$C NMR resonances at 52.2, 52.6, and 52.9 ppm to correspond to the methine carbon in the terminal, linear, and dendritic units (FIG. 12).

The DB of hyperbranched polymers, as described by Fréchet, is determined by the relative abundance of dendritic (D), linear (L), and terminal (T) units, as expressed in Equation 1, $$DB = \frac{D+T}{D+T+L} \quad (1)$$

whereby if all units are linear, DB=0, while for a highly branched polymer, DB approaches 1 as L approaches zero. (Hawker, et al. 1991 *J. Am. Chem. Soc.* 113, 4583.) The deoxybenzoin-containing hyperbranched polyesters obtained from a variety of selected conditions exhibited degrees of branching ranging from 0.14-0.36. Using DCC as the coupling reagent produced polymers with the highest degrees of branching, in reactions performed in DMF at room temperature.

Previously reported hyperbranched polyphenylenes by Kim and Webster achieved degrees of branching of 0.70, while Fréchet observed degrees of branching of 0.55-0.60 for one-step hyperbranched polyesters prepared from an $AB_2$ monomer. (Kim, et al. 1992 *Macromolecules* 25, 5561; Hawker, et al. 1991 *J. Am. Chem. Soc.* 113, 4583.) The modest degrees of branching observed for the deoxybenzoin-based polymers is not surprising due to the unequal reactivity of the monomeric phenols, which leads to departure from ideal reactivity. Nonetheless, characterization shows that significant branching was achieved and in turn the processability of the polymers markedly enhanced relative to linear structures.

Chain-End Functionalization of Polymer 3

A fundamental feature of branched polymers is their large number of chain-ends, which allows for employing post-polymerization reactions to significantly tailor their physical and chemical properties. (Wooley, et al. 1994 *Polym. J.* 26, 187; Voit, et al. 2009 *Chem. Rev.* 109, 5924.) For branched deoxybenzoin polymer 3, esterification of the phenolic chain-ends was achieved by their reaction with monofunctional acid chlorides. For example, simply reacting 3 with excess acetyl chloride, followed by precipitation in methanol, produced the corresponding branched deoxybenzoin polymer with methyl ester chain-ends, while silylation in refluxing hexamethyldisilazane (HMDS) converted the phenols of polymer 3 to TMS ethers, with FTIR spectroscopy (FIG. 13) indicating a complete disappearance of the phenols. The silyl ether-terminated polyester exhibited markedly increased solubility in a variety of common organic solvents, for example a ten-fold greater solubility in DMF (300 mg/mL) over the phenol-terminated version (30 mg/mL), whereas linear deoxybenzoin polyarylates exhibit solubility in DMF at elevated temperature (<3 mg/mL). (Ellzey, et al. 2006 *Marcomolecules* 39, 3553.)

Thermal and Heat Release Properties of Branched Deoxybenzoin Polyesters

Thermal properties of the monomers and polyesters were investigated by thermogravimetric analysis (TGA), differential scanning calorimetry (DSC), and microscale combustion calorimetry (MCC). The TGA data reveals degradation temperature at 5% weight loss to be in the range of 270-330° C. and significant char yields obtained at 750° C., as summarized in Table 1.

As shown in FIG. 5, the $AB_2$ monomer and branched deoxybenzoin-containing polyesters exhibit multi-step degradation and significant char yields (ranging from 30-40%). The branched homopolymer showed the highest char yield values. Table 1 also summarizes the melting temperatures ($T_m$) of the desoxyanisoin derivative and $AB_2$ monomer and the glass transition temperatures ($T_g$) of polymers obtained by DSC.

Microscale combustion calorimetry (MCC) was performed on a highly branched deoxybenzoin polyester, giving heat release profiles such as the representative example shown in FIG. 4, which displays a multi-step decomposition. The peak heat release rate was found to be 117 W/g at 453° C. and a decomposition onset temperature of 397° C. Although the onset temperature is lower than that of some commercial aromatic polyesters, such as poly(ethylene terephthalate) (PET, 414° C.), a 40% char residue after pyrolysis is markedly greater than that of PET (5%). In addition, the total heat release (THR) and heat release capacity (HRC) of branched deoxybenzoin polyester were calculated to be 11.8±0.5 kJ/g and 146±4 J/g-K, respectively. This HRC value is less than half that of PET (366 J/gK) and poly (butylene terephthalate) (PBT, 474 J/gK) and approaches that of polymers with exceptionally low heat release such as chlorine-rich poly(vinyl chloride) (PVC, 138 J/g-K), polyetherketone (PEK, 124 J/g-K), polyetherimide (PEI, 121 J/g-K). (Lyon, et al. 2004 *J. Anal. Appl. Pyrolysis* 71, 27.) Previously synthesized deoxybenzoin-containing linear polyesters exhibited HRCs of 61 J/gK with char yields of 42% determined by thermogravimetric analysis (TGA). The similar char yield obtained from branched deoxybenzoin polyesters (40%) suggests that substitution of the methylene position of deoxybenzoin does not work to the detriment of char formation in polymers. (Ellzey, et al. 2006 *Marcomolecules* 39, 3553; Van Der Waals, et al. 1998 *J. Mol. Catal. A Chem.* 134, 179.)

TABLE 1

Thermal and heat release properties.

| Sample | $T_d$ [a] (° C.) | Char Yield [a] (%) | $T_m$ or $T_g$ [b] (° C.) |
|---|---|---|---|
| $AB_2$ monomer precursor 1 | 273 | 0 | 119 |
| $AB_2$ monomer 2 | 330 | 31 | 154 |
| Polymer 3 | 318 | 40 | 179 |
| Polymer 4 | 310 | 40 | 152 |
| Polymer 5 | 321 | 34 | 121 |
| Polymer 6 | 293 | 31 | 141 |

[a] Obtained by TGA in $N_2$ at a heating rate of 10° C. min$^{-1}$. $T_d$ = 5% weight loss temperature. Char yield = weight loss at 750° C.
[b] Obtained by DSC at a heating rate of 10° C. min$^{-1}$.

$AB_2$ Monomer Integration into $A_2$ and $B_2$ Polymerizations $AB_2$ monomers were also integrated into $A_2$ and $B_2$ polymerizations through a similar carbodiimide coupling, such as with bishydroxydeoxybenzoin (BHDB) and isophthalic acid as shown in FIG. 6. The resulting polymer proved soluble in dimethylformamide, tetrahydrofuran, and dimethylsulfoxide.

Gel permeation chromatography (GPC) was used to characterize the molecular weight of the obtained polymers. The chromatograms are shown in FIG. 7 and the molecular weights summarized in Table 2. The polymers show number-average molecular weights ($M_n$) between 15-24 kDa and polydispersity (PDI, or $M_w/M_n$) ranging from 2.5-3.2.

TABLE 2

Polymer composition and molecular weights

| Sample | [AB$_2$]:[B$_2$]:[A$_2$] | GPC[a] M$_n$ (g mol$^{-1}$) | M$_w$ (g mol$^{-1}$) | Đ |
|---|---|---|---|---|
| Polymer 3 | 1:0:0 | 24000 | 77000 | 3.2 |
| Polymer 4 | 1:1:1 | 15000 | 38000 | 2.5 |

[a] Obtained by GPC performed with DMF as the eluting solvent and molecular weights relative to polystyrene standards.

Additional syntheses integrate deoxybenzoin-containing AB$_2$ monomers into polymerizations containing A$_2$ and B$_2$ monomers, such as the polymerization of commercial monomers isophthaloyl chloride and bisphenol A (BPA). FIG. 8 shows the interfacial polymerization of deoxybenzoin-containing AB$_2$ monomer with isophthaloyl chloride and BPA under phase transfer catalyst conditions to afford a deoxybenzoin-containing branched polyester. BPA can be substituted with other bisphenols, including but not limited to bishydroxydeoxybenzoin (BHDB), to afford polymer. The polymers were insoluble in common organic solvents.

EXPERIMENTAL

Materials.

Desoxyanisoin (98%), benzyl bromide (98%), pyridine hydrochloride (98%), sodium hydride (60% dispersion in mineral oil), N,N'-dicyclohexylcarbodiimide (DCC) (99%), 1,3-diisopropylcarbodiimide (DIPC) (99%), p-toluenesulfonic acid (98.5%), 4-(dimethylamino)pyridine (≥99%), and benzyltriethylammonium chloride (≥99%) were purchased from Aldrich and used as received. 1-Ethyl-3-(3-dimethylaminopropyl) carbodimide hydrochloride (EDC) (>98%) and methyl 4-(bromomethyl) benzoate (>98%) were purchased from TCI Chemical. Sodium hydroxide (≥97%), tetrahydrofuran, and dichloromethane were purchased from Fisher Scientific. Tetrahydrofuran was dried and distilled over sodium/benzophenone ketyl prior to use. (Leonard, et al. Advanced Practical Organic Chemistry Third Edition; CRC Press: Boca Raton, 2013; Chapter 5, pp 77.) Dichloromethane was dried and distilled over calcium hydride. (Kinard, et al. 2012 Nat. Protocols 7, 1219.)

Instrumentation.

$^1$H and $^{13}$C NMR spectra were recorded on a Bruker Ascend™ 500 spectrometer, with chemical shift values expressed in ppm. Relative molecular weights and polydispersities of the branched deoxybenzoin polyesters were determined by GPC with THF eluent relative to linear polystyrene calibration standards. GPC was operated at an eluent flow of 1 mL/min with an Agilent 1260 isocratic pump, an auto sampler, a PL gel guard column (50×7.8 mm$^2$), two PL gel mixed C columns (300 mm×7.8 mm×5 µm), one PL gel mixed D column (300 mm×7.8 mm×5 µm) and an Agilent 1260 refractive index detector. Absolute molecular weights of the branched deoxybenzoin polyesters were determined by GPC (eluting in THF with 0.01 M trimethylamine) operated at a flow rate of 1 mL/min with two PL gel 10 µm mixed-B LS columns, using a DAWN EOS multiangle laser light scattering (MALLS) detector and an EOS refractive index detector; do/dc values were obtained for each injection by assuming 100% mass elution from the columns. Infrared spectra were recorded on a Perkin-Elmer Spectrum One FT-IR spectrometer equipped with an ATR accessory. HRMS-ESI data were obtained on an Orbitrap Fusion mass spectrometer and HRMS-EI data were obtained on a JEOL-700 MStation in the mass spectrometry facility at UMass Amherst. Thermogravimetric analysis (TGA) was performed on a TA Instruments Q50 machine at a heating rate of 10° C./min in a N$_{2(g)}$ atmosphere. Microscale combustion calorimetry (MCC) was employed to determine the heat release properties using an experimental design stated in ASTM D7309-13, Method A. (ASTM D7309-13, *Standard Test Method for Determining Flammability Characteristics of Plastics and Other Solid Materials Using Microscale Combustion calorimetry*, Test Method A, ASTM International, West Conshohocken, Pa., 2013.) Experiments were conducted in an 80 cm$^3$/min stream of nitrogen at a heating rate of 1° C./s from 75 to 900° C. The anaerobic thermal degradation products were combined with a 20 cm$^3$/min stream of oxygen gas in a furnace at 900° C.

Methyl Benzoate Substituted Desoxyanisoin (1).

Desoxyanisoin (18.7 g, 73.0 mmol) was dissolved in anhydrous THF (180 mL) in a flame-dried, two-neck round-bottom flask equipped with a stir bar, reflux condenser, and N$_{2(g)}$ inlet. Sodium hydride (2.62 g, 109 mmol) was added slowly and the mixture was stirred at 23° C. for 2 hours. A solution of methyl 4-(bromomethyl) benzoate (25.0 g, 109 mmol) in anhydrous THF (45 mL) was added dropwise and the resulting suspension was heated to reflux for 8 hours. The mixture was cooled to 23° C., poured over crushed ice, and washed with ethyl acetate (3×). The organic layers were combined and dried over sodium sulfate, filtered, and concentrated. The crude product was stirred in diethyl ether for 30 minutes at 30° C., filtered, then gently washed with diethyl ether. The desired product was obtained as a white powder after drying under vacuum (22.9 g, 86%). $^1$H NMR (500 MHz, DMSO-d$_6$, δ): 7.98 (d, J=8.8 Hz, 2H; Ar H), 7.79 (d, J=8.1 Hz, 2H; Ar H), 7.34 (d, J=8.1 Hz, 2H; Ar H), 7.20 (d, J=8.6 Hz, 2H; Ar H), 6.95 (d, J=8.8 Hz, 2H; Ar H), 6.80 (d, J=8.6 Hz, 2H; Ar H), 5.14 (t, J=7.5 Hz, 1H; CH), 3.80 (s, 3H, OCH$_3$), 3.77 (s, 3H, OCH$_3$), 3.66 (s, 3H, OCH$_3$), 3.45 (dd, J=13.7, 7.7 Hz, 1H; CH$_2$), 3.03 (dd, J=13.7, 7.3 Hz, 1H; CH$_2$). $^{13}$C NMR (126 MHz, DMSO-d$_6$, δ): 197.18, 166.12, 163.03, 158.09, 145.77, 131.01, 130.92, 129.40, 129.18, 128.85, 127.30, 114.10, 113.83, 55.45, 54.90, 51.91, 51.83. HRMS (ESI, m/z): [M+Na]$^+$ calcd for C$_{25}$H$_{24}$O$_5$, 427.1523; found, 427.1516.

Benzoic Acid Substituted Bishydroxydeoxybenzoin (2).

To a two-neck round-bottom flask equipped with a stir bar, condenser, and N$_{2(g)}$ inlet, compound 1 (21.3 g, 49.9 mmol) and pyridine hydrochloride (100.0 g, 866 mmol) were added and heated to 200° C. for 6 hours. The mixture was cooled to 23° C. and the crude product was dissolved in ethyl acetate and washed three times with water. The organic layer was dried over magnesium sulfate, filtered, and concentrated. The residue was washed with diethyl ether and dried under vacuum to yield 2 as a white solid (14.8 g, 76% yield). $^1$H NMR (500 MHz, DMSO-d$_6$, δ): 12.76 (s, 1H, COOH), 10.31 (s, 1H, Ar OH), 9.29 (s, 1H, Ar OH), 7.86 (d, J=8.7 Hz, 2H; Ar H), 7.77 (d, J=8.1 Hz, 2H, Ar H), 7.29 (d, J=8.1 Hz, 2H; Ar H), 7.09 (d, J=8.4 Hz, 2H; Ar H), 6.76 (d, J=8.7 Hz, 2H; Ar H), 6.64 (d, J=8.4 Hz, 2H; Ar H), 5.00 (t, J=7.4 Hz, 1H; CH), 3.41 (dd, J=13.6, 6.9 Hz, 1H; CH$_2$), 2.99 (dd, J=13.6, 6.9 Hz, 1H; CH$_2$). $^{13}$C NMR (126 MHz, DMSO-d$_6$, δ): 197.01, 167.26, 161.97, 156.21, 145.49, 131.17, 129.55, 129.22, 129.13, 129.03, 128.40, 127.61, 115.46, 115.17, 51.83. HRMS (ESI, m/z): [M+Na]$^+$ calcd for C$_{22}$H$_{18}$O$_5$, 385.1053; found, 385.1046.

General Procedure for the Preparation of Branched Deoxybenzoin Polyester 3.

Compound 2 (1.00 g, 2.76 mmol), 4-(dimethylamino)pyridinium 4-toluenesulfonate (DPTS) (0.162 g, 0.552 mmol), and anhydrous DMF (3.70 mL) were added to a flame-dried two-neck round-bottom flask and the mixture was stirred under $N_{2(g)}$ for 30 minutes at 23° C. 1-Ethyl-3-(3-dimethylaminopropyl) carbodiimide hydrochloride (EDC) (0.688 g, 3.59 mmol) was added and the mixture was stirred for 24 hours. The mixture was filtered and precipitated into methanol (~50 mL). The obtained polymer was recovered by filtration, washed with aqueous lithium chloride and 5% HCl aqueous solution, followed by drying under vacuum to yield a white solid (81% yield). $^1$H NMR (500 MHz, DMSO-$d_6$, δ): 10.46 (s, Ar OH), 10.39 (s, Ar OH), 9.36 (s, Ar OH), 9.29 (s, Ar OH), 8.77 (Ar H), 8.45 (Ar H), 8.15 (Ar H), 7.95 (Ar H), 7.90 (Ar H), 7.42 (Ar H), 7.35 (Ar H), 7.12 (Ar H), 7.07 (Ar H), 6.71 (Ar H), 6.65 (Ar H), 5.43 (Ar H), 5.19 (CH), 5.05 (CH), 4.50 (CH), 4.49, 4.27, 4.26, 3.57, 3.46, 3.22, 3.10. $^{13}$C NMR (126 MHz, DMSO-$d_6$, δ): 53.29 (CH, dendritic), 52.11 (CH, linear), 51.59 (CH, terminal).

Benzyl-Substituted Desoxyanisoin (4).

A flame-dried, two-neck round-bottom flask equipped with a stir bar, reflux condenser, and $N_{2(g)}$ inlet was charged with a solution of desoxyanisoin (20.0 g, 78.0 mmol) in anhydrous THF (195 mL). Sodium hydroxide (4.70 g, 118 mmol) was added and the mixture was allowed to stir at 23° C. for 2 hours. A solution of benzyl bromide (13.9 mL, 117 mmol) in anhydrous THF (40 mL) was added dropwise and the mixture was heated to reflux for 8 hours. The mixture was then cooled to 23° C., poured over ice, and extracted three times with ethyl acetate. The organic phases were combined and washed with water, dried with magnesium sulfate, filtered, and concentrated. The crude product was purified by stirring in diethyl ether at 30° C. for 30 minutes, followed by filtration to recover 4 as a white solid, which was dried under vacuum to give 22.1 g (82% yield). $^1$H NMR (500 MHz, DMSO-$d_6$, δ): 7.97 (d, J=8.9 Hz, 2H; Ar H), 7.24 (d, J=8.6 Hz, 2H; Ar H), 7.18 (m, 4H; Ar H), 7.11 (d, J=13.1 Hz, 1H; Ar H), 6.95 (d, J=8.8 Hz, 2H, Ar H), 6.82 (d, J=8.6 Hz, 2H; Ar H), 5.11 (t, J=7.4 Hz, 1H; CH), 3.78 (s, 3H, $CH_3$), 3.67 (s, 3H, $CH_3$), 3.39 (dd, J=8.1, 13.7 Hz, 1H; $CH_2$), 2.95 (dd, J=6.8, 13.7 Hz, 1H; $CH_2$). $^{13}$C NMR (126 MHz, DMSO-$d_6$, δ): 197.45, 163.01, 158.06, 139.86, 131.41, 130.90, 129.21, 128.98, 128.96, 127.99, 125.85, 114.07, 113.85, 55.47, 54.93, 52.10. HRMS (ESI, m/z): [M+Na]$^+$ calcd for $C_{23}H_{22}O_3$, 369.1468; found, 369.1462.

Benzyl-Substituted Bishydroxydeoxybenzoin (5).

Compound 4 (5.00 g, 14.0 mmol) and pyridine hydrochloride (10.0 g, 87.0 mmol) were combined in a two-neck round-bottom flask equipped with a stir bar, reflux condenser, and $N_{2(g)}$ inlet in a preheated oil bath at 200° C. for 6 h. The mixture was cooled to 23° C. and water was added. The solution was washed with ethyl acetate three times. The organic layers were combined, dried over sodium sulfate, filtered, and concentrated. The crude product was washed with diethyl ether, filtered, and dried under vacuum to afford compound 5 (3.92 g, 91%). $^1$H NMR (500 MHz, DMSO-$d_6$, δ): 10.29 (s, 1H; OH), 9.26 (s, 1H; OH), 7.85 (d, J=8.6 Hz, 2H; Ar H), 7.6 (m, 4H; Ar H), 7.09 (d, J=8.2 Hz, 2H; Ar H), 6.74 (d, J=8.6 Hz, 2H; Ar H), 6.62 (d, J=8.3 Hz, 2H; Ar H), 4.95 (t, J=7.4 Hz, 1H; CH), 3.36 (dd, J=13.7, 7.1 Hz, 1H; $CH_2$), 2.89 (dd, J=7.1, 13.7 Hz, 1H; $CH_2$). $^{13}$C NMR (126 MHz, DMSO-$d_6$, δ): 197.24, 161.93, 156.16, 140.07, 131.13, 129.88, 129.13, 128.97, 127.97, 127.77, 125.79, 115.43, 115.17, 52.09. HRMS (ESI, m/z): [M+Na]$^+$ calcd for $C_{21}H_{18}O_3$, 318.1155; found, 318.1148.

Mono-Benzoate Ester (6).

A flame-dried, two-neck round-bottom flask equipped with a stir bar and $N_{2(g)}$ inlet was charged with compound 5 (0.5 g, 1.57 mmol), DPTS (0.09 g, 0.314 mmol), benzoic acid (0.19 g, 1.57 mmol), and anhydrous DMF (5.2 mL). The mixture was allowed to stir at 23° C. for 20 minutes, then DCC (0.42 g, 2.04 mmol) was added. After 20 minutes, the mixture was filtered, gently washed with DMF, and added to ether (15 mL). The organic layer was washed three times with a 5% lithium chloride aqueous solution (15 mL). The organic layer was collected and dried with sodium sulfate, filtered, and concentrated. The solid residue was purified by column chromatography using a 70:30 ethyl acetate:hexanes mixture. Yield (0.66 g, 72%). $^1$H NMR (500 MHz, DMSO-$d_6$, δ): 9.34 (s, 1H; OH), 8.12 (m, 4H; Ar H), 7.75 (t, J=7.5 Hz, 1H; Ar H), 7.60 (m, 2H, Ar H), 7.39 (d, J=9.0 Hz, 2H; Ar H), 7.20 (m, 5H; Ar H), 7.13 (d, J=8.5 Hz, 2H; Ar H), 6.68 (d, J=8.0 Hz, 2H; Ar H), 5.13 (t, J=7.4 Hz, 1H; CH), 3.41 (dd, J=7.9 Hz, 1H; $CH_2$), 2.96 (dd, J=6.9 Hz, 1H; $CH_2$) $^{13}$C NMR (126 MHz, DMSO-$d_6$, δ): 206.92, 198.57, 168.60, 164.59, 156.82, 154.56, 140.23, 134.71, 134.39, 130.77, 130.34, 129.75, 129.46, 129.02, 128.46, 126.34, 122.69, 116.05, 53.08. HRMS (EI, m/z): [M] calcd for $C_{28}H_{22}O_4$, 422.1518; found, 422.1536.

Bis-Benzoate Ester (7).

To a two-neck round-bottom flask equipped with a stir bar and $N_{2(g)}$ inlet compound 5 (0.5 g, 1.57 mmol) was added a 10% sodium hydroxide in water solution followed by benzyl triethyl ammonium chloride (18 mg, 0.08 mmol). To this solution was added benzoyl chloride (0.36 mL, 3.14 mmol) in dichloromethane (15.7 mL). The mixture was stirred vigorously at 23° C. for one hour, then the solution was concentrated, dissolved in ethyl acetate (15 mL), and washed with water (15 mL) three times. The organic layer was collected, dried with sodium sulfate, filtered, and concentrated to afford compound 7. (0.83 g, 90%). $^1$H NMR (500 MHz, DMSO-$d_6$, δ): 8.17 (m, 9H; Ar H), 7.95 (m, 1H; Ar H), 7.82 (m, 2H; Ar H), 7.74 (m, 2H; Ar H), 7.65 (m, 8H; Ar H), 7.45 (d, J=8.6, 2H; Ar H), 7.23 (d, J=8.7, 2H; Ar H), 7.14 (t, J=6.9, 1H; Ar H), 5.37 (t, J=7.4, 1H; CH), 3.49 (dd, J=7.9, 5.9, 1H; $CH_2$), 3.08 (dd, J=7, 6.8, 1H; Ar H). $^{13}$C NMR (126 MHz, DMSO-$d_6$, δ): 198.45, 167.79, 164.89, 164.57, 162.82, 154.81, 149.98, 139.87, 137.11, 135.62, 134.73, 134.52, 134.18, 133.33, 130.85, 130.36, 130.21, 129.86, 129.81, 129.73, 129.48, 129.43, 129.33, 129.03, 129.01, 128.56, 128.50, 126.51, 122.84, 122.67, 53.07. HRMS (EI, m/z): [M] calcd for $C_{35}H_{26}O_5$, 526.1780; found, 526.1806.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A compound having the structural formula of:

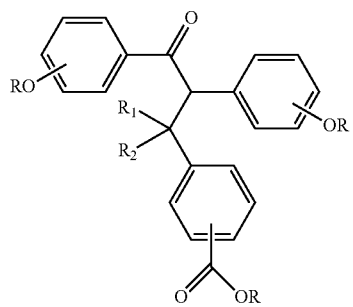

wherein each of R, $R_1$ and $R_2$ is independently selected from H and ($C_1$-$C_6$) alkyl groups.

2. The compound of claim 1, wherein each R is a ($C_1$-$C_6$) alkyl.

3. The compound of claim 2, wherein each R is a methyl.

4. The compound of claim 1, wherein each R is H.

5. The compound of claim 1, wherein each of $R_1$ and $R_2$ is H.

6. The compound of claim 1, wherein at least one of $R_1$ and $R_2$ is a ($C_1$-$C_6$) alkyl group.

7. The compound of claim 1, wherein the compound has the following structural formula:

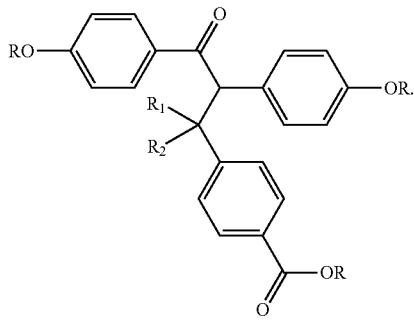

8. A polymer prepared from a compound having the structural formula of:

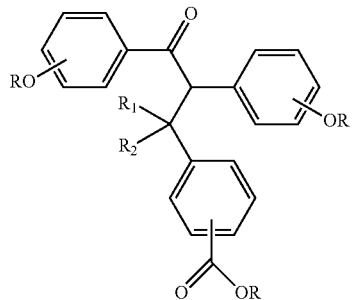

wherein each of R, $R_1$ and $R_2$ is independently selected from H and ($C_1$-$C_6$) alkyl groups.

9. The polymer of claim 8, wherein the compound has the following structural formula:

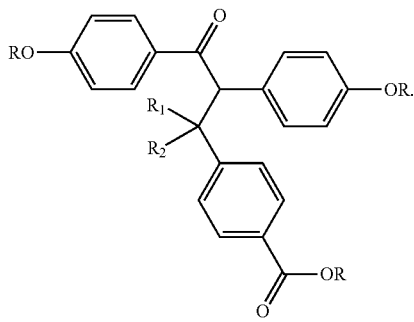

10. A polymer comprising a structural unit of the formula:

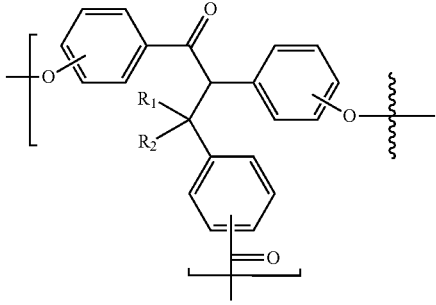

wherein each of $R_1$ and $R_2$ is independently selected from H and $(C_1-C_6)$ alkyl groups.

11. The polymer of claim 10, wherein each of $R_1$ and $R_2$ is H.

12. The polymer of claim 10, wherein at least one of $R_1$ and $R_2$ is a $(C_1-C_6)$ alkyl group.

13. The polymer of claim 10, wherein the structural unit has the following structural unit:

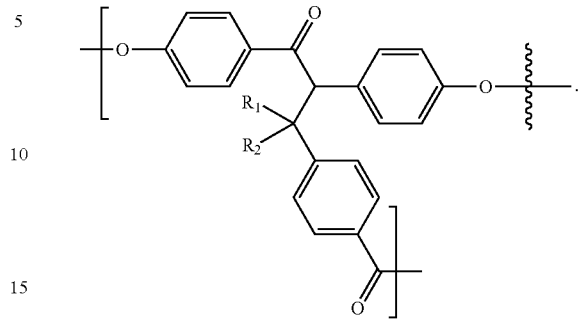

14. The polymer of claim 10, wherein the polymer is a homopolymer.

15. The polymer of claim 10, wherein the polymer is a copolymer.

16. The polymer of claim 10, having a molecular weight $M_w$ from about 1,000 to 100,000.

17. A resin composition comprising a polymer of claim 10.

18. A flame-retardant additive comprising a polymer of claim 10.

19. A material comprising the flame-retardant additive of claim 18.

20. A minimal- or non-flammable material comprising a polymer of claim 10.

* * * * *